United States Patent
Sun

(10) Patent No.: US 9,956,367 B1
(45) Date of Patent: May 1, 2018

(54) LARYNGASCOPE FREE AIRWAY DEVICE

(71) Applicant: Yang Sun, San Francisco, CA (US)

(72) Inventor: Yang Sun, San Francisco, CA (US)

( * ) Notice: Subject to any disclaimer, the term of this patent is extended or adjusted under 35 U.S.C. 154(b) by 457 days.

(21) Appl. No.: 14/589,975

(22) Filed: Jan. 5, 2015

Related U.S. Application Data

(60) Provisional application No. 61/964,419, filed on Jan. 6, 2014.

(51) Int. Cl.
| | | |
|---|---|---|
| *A61M 16/04* | (2006.01) | |
| *A61B 1/00* | (2006.01) | |
| *A61B 1/267* | (2006.01) | |

(52) U.S. Cl.
CPC ..... *A61M 16/0497* (2013.01); *A61B 1/00082* (2013.01); *A61B 1/00137* (2013.01); *A61B 1/00165* (2013.01); *A61B 1/267* (2013.01); *A61M 16/0415* (2014.02); *A61M 16/0429* (2014.02); *A61M 16/0459* (2014.02); *A61M 16/0463* (2013.01); *A61M 2210/0656* (2013.01); *A61M 2210/105* (2013.01)

(58) Field of Classification Search
CPC .......... A61M 16/0497; A61M 16/0454; A61M 16/0456; A61M 16/0459; A61M 16/0429; A61M 16/0463; A61M 2210/0656; A61B 1/00082; A61B 1/00137; A61B 1/267
See application file for complete search history.

(56) References Cited

U.S. PATENT DOCUMENTS

| | | | | |
|---|---|---|---|---|
| 5,632,271 | A * | 5/1997 | Brain | A61M 16/04 128/207.14 |
| 5,682,880 | A * | 11/1997 | Brain | A61M 16/0409 128/200.26 |
| 5,896,858 | A * | 4/1999 | Brain | A61M 16/04 128/200.26 |
| 6,240,922 | B1 * | 6/2001 | Pagan | A61M 16/04 128/200.26 |
| 6,631,720 | B1 * | 10/2003 | Brain | A61M 16/04 128/207.14 |
| 8,622,060 | B2 | 1/2014 | Cook | |
| 8,631,796 | B2 | 1/2014 | Cook | |
| 8,714,159 | B2 | 5/2014 | Baska | |
| D710,990 | S | 8/2014 | Brain | |
| 8,863,746 | B2 | 10/2014 | Totz | |

(Continued)

*Primary Examiner* — Timothy J Neal
(74) *Attorney, Agent, or Firm* — David Olsen; Olsen Patent Law

(57) ABSTRACT

An airway device configured for intubation under blind or optionally under indirect vision of a fiber optic scope. It also configured to be used as a supraglottic airway device supporting external breathing or anesthesia circuits. The device comprises a tube system with expansion projections, a base, one or more inflation balloons, and a gastric suction tube. The device can include a stylet to guide endotracheal tube during intubation. The tube system can include an air tube and fiber-optic-probe tube. The balloon system can move the end of the tube system anteriorly to align it with the laryngeal opening. The balloon system can seal the airway leakage for low positive pressure ventilation for the device to operate as a supraglottic airway device. The inflation balloon and expansion projection can displace tissue that can block the airway path. The base can carry esophageal gastric drainage tube to the upper esophageal sphincter to block and drain gastric content regurgitation.

26 Claims, 9 Drawing Sheets

(56) References Cited

U.S. PATENT DOCUMENTS

2008/0276936 A1* 11/2008 Cook ................... A61M 16/04
                                                        128/204.18
2014/0309494 A1* 10/2014 Molnar ................. A61B 7/003
                                                        600/109

* cited by examiner

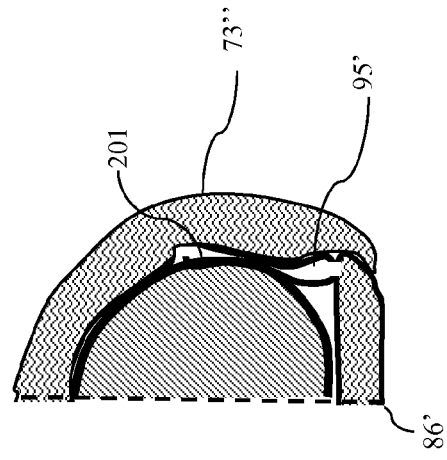
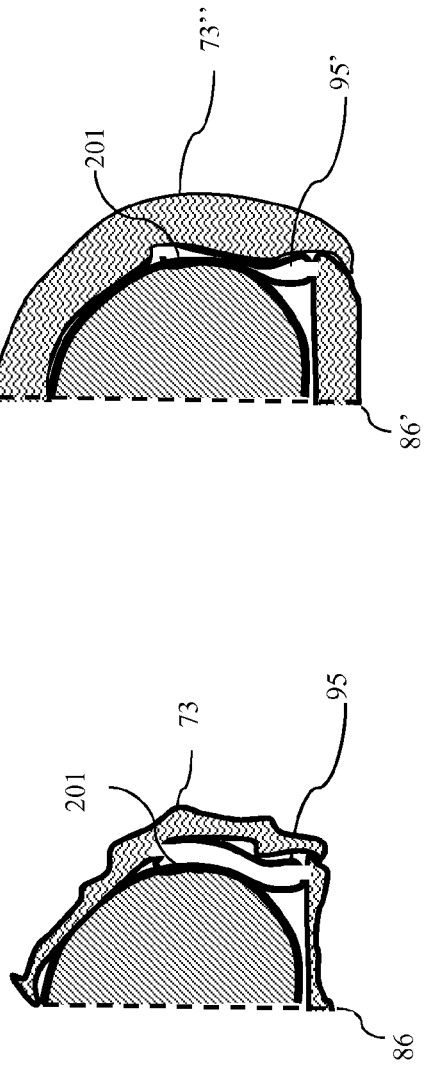
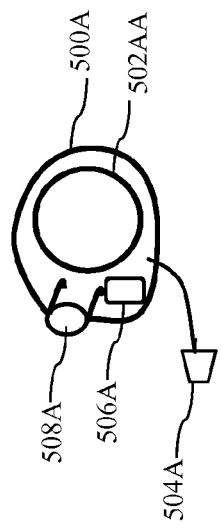

LARYNGASCOPE FREE AIRWAY DEVICE

CROSS REFERENCE TO OTHER APPLICATIONS

This application claims priority under 35 U.S.C. § 119(e) of the U.S. provisional patent application Ser. No. 61/964,419 filed on Jan. 6, 2014 entitled "Laryngoscope Free Airway." The provisional patent application Ser. No. 61/964,419 filed on Jan. 6, 2014 entitled "Laryngoscope Free Airway" is hereby incorporated by reference.

FIELD OF INVENTION

The present invention relates to medical airway management devices and methods for blindly, rapidly and gently intubating people and animals in routine surgical cases, intensive care unit, and emergency resuscitation. The present invention is designed to be easily used by with minimal training of medical personal, in in-hospital, pre-hospital, surgical clinical, not limited to specialized medical specialties.

Further, the invention relates to airway devices that supports a visualization system, including fiber-optic imaging systems, for visualization of the larynx inlet during and after intubation if desired by an operator but it is not mandatory. The invention also relates to devices that can serve as an independent supraglottic airway device for spontaneous and artificial ventilation of the lungs if intubation is not desired. Further, the invention relates to devices that provide access to suction the larynx inlet area to prevent aspiration. Additionally, the present invention related to devices that provide an access to drainage and suction esophageal and gastric content by pre-built in tube. Further present invention provides alternative easy access for ENT (Ear Nose and Throat) surgeons to the larynx inlet area for inspection with a fiber-optic endoscope, flexible forceps retrieving of a foreign body, and access for biopsies.

What is need is devices and systems that provides blind, rapid, and gentle intubation of people and animals, that supports visualization systems for the larynx inlet before, during and after intubation, devices that can function as an independent supraglottic airway device, and devices that provide ENT surgeon an access to the larynx inlet area for inspection, retrieval of a foreign body, suctioning and for biopsies.

BACKGROUND

When a person stop breathing, it is imperative that effective ventilation be instituted as soon as possible. A blade laryngoscope is commonly employed to place an ETT (endotracheal tube) into a person's trachea. However, a blade laryngoscope has significant patient risks. These include dental injury, airway soft tissue injury, and further injury to a patient's with a neck injury caused by neck manipulation during blade insertion. Further, visualization of vocal cords can be difficult or impossible. A result can be an endotracheal tube that is misguided into a patient's esophagus. Such improper intubation, if not quickly corrected can have fatal consequences.

There are many other supraglottic airway (SGA) devices being used in the spontaneous breathing of anesthetized patients, during recovery from anesthetics, weaning of some patients in intensive care unit, or for airway management during resuscitation. Examples of prior art devices include but are not limited to supraglottic ventilation devices, Ballooned Oro-pharyngeal airway, LMA, and Combi-tube devices.

There are many prior art devices used in endotracheal intubation. These include metal Macintosh and Miller laryngoscope blade, many types of video larynscopes such as the Glidescope, Mcgrath, Airtraq, C-Mac, Berci-Kaplan DCI, Pentax Airway Scope, Truview EVO, and LMA fast track. These devices rely on obtaining direct or indirect view of the epiglottis and glottis inlet during intubation. However, a variety of trauma and clinical settings can make direct or indirect visual observation very difficult if not impossible. These include an unstable cervical spine injury, airway bleeding or heavy secretion, an obese patient, or a patient that needs intubation in an unusual position such as a person in a car wreck.

Recently, there are devices introduced for blind placement of an endotrachecal tube. Examples of these include a laryngeal mask airway (LMA), U.S. Pat. No. 4,509,514 in 1985 by Brain and an intubation laryngeal mask airway (ILMA), U.S. Pat. No. 5,303,697 1994 by Brain. However, these LMA blind intubation devices are easily positioned incorrectly. Even when ventilation can still be carried out, an LMA can be inefficient and increase the risk of aspiration. Further, even when this blind intubation device is correctly inserted and positioned, sliding an endotracheal tube alone the elongated air tube into a trachea is difficult. Another problem with these devices is that the device can push or catch the epiglottis moving it over the glottis and obstruct the airway. Another disadvantage of an LMA is that it often poorly seals making it easier for regurgitation and aspiration.

IMLA was especially designed for blind intubation. One ILMA patent, U.S. Pat. No. 5,896,858 by Brain 1999, was designed to insert an endotracheal tube though an LMA without visualization. This design has achieved limited acceptance and has a number of limitations.

First, the ILMA has a metal handle with a pronounced curved region making it difficult to insert into a patient's mouth. It usually requires muscle relaxants drugs in order to open a patient's mouth wide enough to prevent tissue damage. Second, the ILMA relies on precise positioning and perfect alignment of the epiglottis with the recessed epiglottis elevation bar so that the epiglottis elevation bar would raise the epiglottis out of the way of an advancing endotracheal tube. Such precise position is often hard to achieve. One problem that the ILMA can exhibit is that the tip can become folded at the back of the oropharynx, or the epiglottis could be folded down, or the endotracheal tube can become lodged against the edge of vocal cords. These problems can make the passing of an endotracheal tube very difficult. And in addition, ILMA requires a special endotracheal tube which is inconvenient and more costly. One prior art ILMA embodiment, Pagan, U.S. Pat. No. 5,983,897 1999 added a plate projection to the tip of an inflatable balloon to aid insertion. This stiff leading tip increases the risk of soft tissue injury during the insertion. Additionally, the tip projects outwardly from the LMA structure thereby lengthening the device and thereby increasing the difficulty of inserting the device. In the prior art patent U.S. Pat. No. 8,128,071, optical fibers were added to gain visualization of the laryngeal anatomy, but this device also suffers from the limitations stated above.

Prior art also discloses guides for intubation. U.S. Pat. No. 4,832,020, "Tracheal Intubation Guide", 1989 by Augustine and U.S. Pat. No. 6,672,305 "Shallow Throat Orotracheal Intubation Guide" and RE39,508 E, 2007 "Blind Orolaryngeal and Oroesophageal Guiding Aiming Device" disclose a tracheal intubation guide which sits above the glottis. However, there is no assurance of stable alignment of the device with respect to the laryngeal opening. Therefore, an endotracheal tube can be misguided and cause incorrect intubation and laryngeal trauma.

In another prior art patent by David D. Alfery, U.S. Pat. No. 7,040,312, 2006, "Perilaryngeal Oral Airway" discloses an oral airway that can be used to guide an endotracheal tube into a trachea by axially advancing the endotracheal tube through a gap defined by the material forming the grate of the wedge-shaped housing. But this depends on precisely positioning the wedge shaped housing, that the epiglottis slides up the grate and into abutment with the anterior wall of wedge-shaped housing. These requirements make intubation very difficult to be achieved quickly and reliably.

In another prior art, "Method of manufacturing an airway device", by Muharmmed Aslam Nasir, U.S. Pat. No. 8,778, 248, Jul. 15, 2014, a laryngeal airway device tries to provide a precise mirror image laryngopharyngeal framework, and thus provide an anatomical fit over the laryngeal inlet. However the anatomy of laryngeal pharynx is highly variable and it is very difficult to have an universal device to fit each individual's anatomy. Therefore, a poor air seal is often achieved which easily causes aspiration. Further, if positive ventilation applied, air can easily flow into stomach resulting in artificial ventilation failure and aspiration.

The use of a flexible fiber-optic intubation of the trachea has been used in medical practice for decades which allows for placement of an endotracheal tube with minimal manipulation of the patients airway. While this technique had been considered the gold standard in case of awake intubation, often the tip of the fiber optic scope is touching and bent against the wall of a patient's airway obstructing the view. Additionally, secretions and blood often block the view of the tip of fiber optic scope, all those reasons easily cause the intubation to fail. Further, this technique is time consuming not suitable in emergence situations and requires significant skill and training.

All of these prior art devices have different disadvantages, complications and co-morbidity, and these devices can require significant training and can be expensive to manufacture.

One objective of the various embodiments of this invention is to minimize and mitigate the complication, co-morbidity, and training time for airway devices. Further, it is an objective of embodiments of this invention to provide a new method for vocal cord inspection, biopsy, retrieval of foreign bodies, and use in various otolaryngology.

BRIEF DESCRIPTION OF THE DRAWINGS

FIG. 5A is a view of the cuff's auto-pressure limiting mechanism with the first balloon deflated.

FIG. 5B is a view of the cuff's auto-pressure limiting mechanism with the first balloon inflated FIG. 6 is a top view of an embodiment of a LFA adaptor cap.

SUMMARY OF INVENTION

Figure 1:
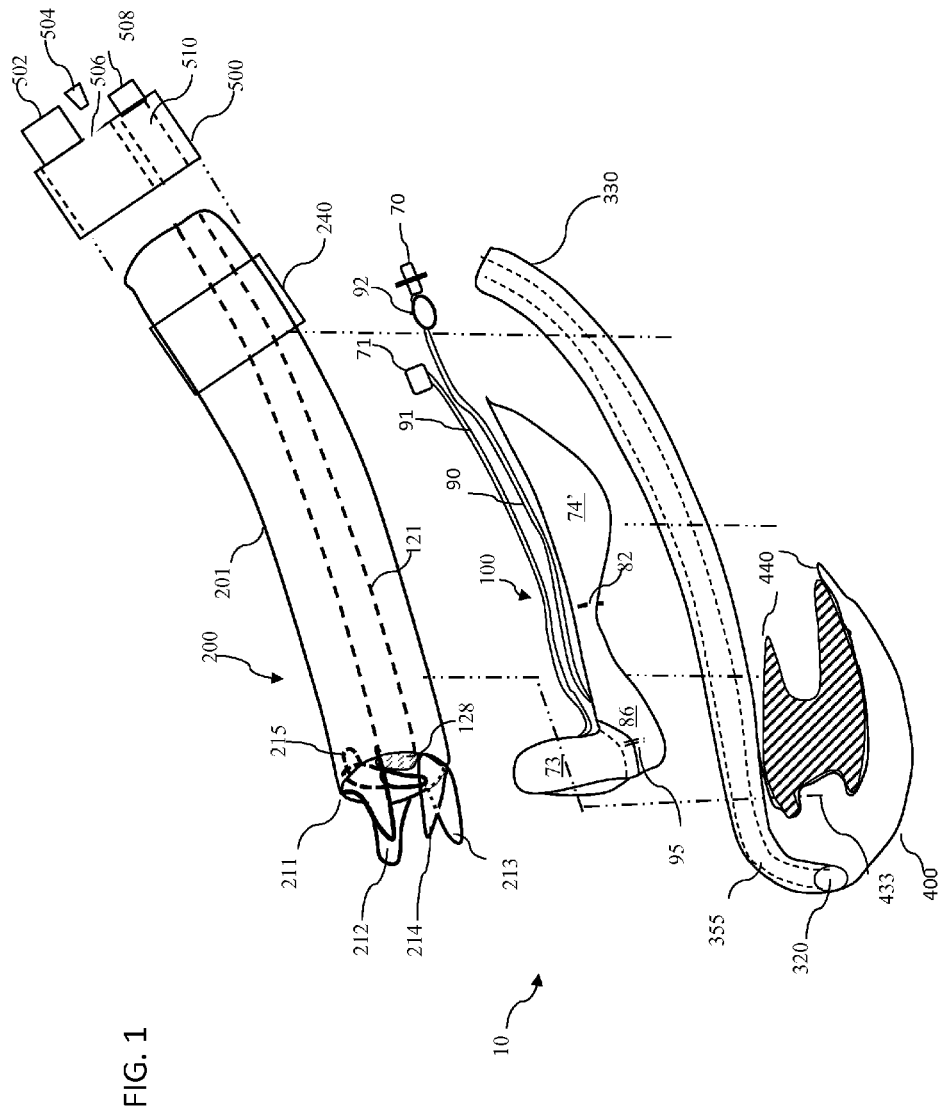
FIG. 1 is an exploded view of the first embodiment of the LFA.

Various invention embodiments provide blind, rapid, and gentle patient and animal intubation, free of using a laryngoscope.

In one embodiment, the LFA (Laryngoscope Free Airway) is comprised of a tube system with one or more airway expansion projections coupled to the air tube distal end, a balloon system and a base.

The tube system is comprised of an air tube that is open at both the proximal and distal ends, and can include a fiber-optic-probe tube that is open on the proximal end and closed transparent distal end. The distal end is transparent and provides substantially distortion free transmission of light. Preferably, the air tube and fiber-optic-probe tube are not in communication with each other to prevent contamination of a fiber-optic-probe tube and thus the fiber-optic probe when inserted into the tube.

The base is coupled towards the mid or distal segment of the tube system and the leading edge of the base can be configured to reach the upper esophageal sphincter which may be able to block regurgitation. The base can also serve as a platform for an esophageal gastric drainage tube which can be connected to a suction device. Alternatively, an oral gastric tube can be passed through the oral-gastric-drainage tube, through the esophageal sphincter and into the stomach to empty its contents. The end of the air tube is configured with one or more air expansion projections. In their nature relaxed position, the four projections are orientated parallel with the air tube longitudinal axis. The projections provide a guide for an advancing endotracheal tube and can push away tissue blocking the airway.

In one embodiment, the distal portion of the base includes a securing means, a barb, to hold the expansion projections and an EEB #1 (first epiglottis elevation bar) in flexed and inwardly bent position, or restrained position just before and during the insertion of the LFA and until inflation of the balloon system.

In further embodiment, the device is configured with a first inflatable balloon. The first balloon is located between the base and the tube system distal segment. Preferably the first balloon is configured to impart an anterior movement of the air tube distal segment when inflated and to release one or more projections from the base securing means when inflated.

In another embodiment, the device includes a cuff inflatable balloon surrounding the right, top, and left sides, wrapping around the distal end of the tube system. The cuff balloon will seal the space between end of the tube system and hypo-pharynx, and can move the end of air tube into better alignment with a glottic opening. The EEB #1 can be one of the expansion projections that are part of the distal end air tube wall and located at the top of the air tube. The EEB#2 is tucked inside lumen of end air tube. In a further embodiment, the device includes a back support balloon (BSB), also referred to as the third balloon, is coupled to the back of the tube system. An inflation injection port and an injection tube are in communication with first balloon. When air, gas or liquid is injected into first balloon, the air, gas or liquid will also flow to the cuff and third balloon by a low rate communication means. The air or liquid flows from first balloon to cuff balloon through a narrow relatively soft plastic tube. This communication means is referred to as a first-cuff balloon communication tube. The communication between first and third balloon (BSB) is through a relatively narrow passage running under or between the between the two legs of the base. Details on the base components are described below. As inside of pressure of cuff balloon increases to predetermined level, the cuff balloon compresses the first-cuff balloon communication tube between the cuff balloon and the air tube and blocks the first-cuff balloon communication tube. This configuration provides for a pressure difference between the first and cuff balloon. Even though the BSB inflates slower than first balloon, the inside pressure will be eventually equalize. This is the pressure limiting and self-adjusting mechanism of the balloon system. Alternatively there could have another inflation injection line to connect with one of the three balloons to achieve same goal.

In one embodiment, the device includes stylet used in conjunction with an endotracheal tube. The stylet comprises a rod made of a semi-rigid plastic material with a sickle shaped tip with a very slippery surface at distal end of a rod which is inserted into an endotracheal tube or the air tube depending how an operator proceeds with intubation. This detail will describe later. The sickle tip of stylet is moved around to locate the opening of the vocal cords. Then once the stylet is through the vocal cords, the stylet's rod acts as a guide for sliding an endotracheal tube down though the vocal cords.

As will be realized, the invention is capable of other and different embodiment and its several detail are capable of modification in various respects, all without departing from the invention. Accordingly, the drawing and description are to be regarded as illustration to nature and not in a restrictive or limitation sense.

DETAILED DESCRIPTION OF THE INVENTION

The following description of the invention is provided as an enabling teaching of the invention. Those skilled in the relevant art will recognize that many changes can be made to the embodiment described, while still attaining the beneficial results of the present invention. It will also be apparent that some of the desired benefits of the present invention can be attained by selecting some of the features of the present invention without utilizing other features. Accordingly, those skilled in the art will recognize that many modifications and adaptations to the present invention are possible and can even be desirable in certain circumstances, and are a part of the present invention. Thus, the following description is provided as illustrative of the principles of the present invention and not a limitation thereof.

For the purpose of the drawings and description, the use of the word "front" refers to the proximal end of a Laryngoscope Free Airway intubation device, herein after LFA. The use of the word "top" refers to the side of the LFA opposing the base. The use of the word "bottom" refers to the side of the LFA to which the base is attached. The use of the word "back" refers to the side of the tube system which the base is attached. For the purpose of this description, the term "relaxed" means the position that an component would take when no forces are placed on the component. Further, the use of the term "communication" is used to mean a path for air, gas, or fluid to flow.

The Laryngoscope Free Airway intubation device, herein after LFA, provides an airway conduit for people, patients, and other mammals for the insertion of an endotracheal tube or used as an independent supraglottic airway (SGA) device. Further it can provide additional functions and features. The LFA can be configured with a lumen for fiber-optic probe viewing of a glottis opening. The LFA can provide ENT surgeons access to the Larynx area and vocal cords. Additionally, the LFA can be configured with an esophageal gastric drainage tube (EGDT). The EGDT can be connected to an independent suction device. Alternatively, the EGDT ca be used to delivery an oral-gastric tube through the esophagus and into the stomach and then connected an independent suction device. The leading edge of the base of LFA may be used to block gastric content regurgitation.

The LFA is comprised of a base, a tube system, one or more expansion projections, a balloon system, an esophageal gastric drainage tube, a stylet, or a combination thereof. These components can be configured in different configurations and combinations for different embodiments of the invention.

The base is provides multiple functions. The base tip can press against a person's upper epiglottis sphincter to block and drainage of esophageal and gastric content. It can be configured with an EGDT for managing esophageal and gastric contents. It can be configured a means to restrain or hold the airway expansion projections in an inward bended restrained position and release the expansion projections to move to a relaxed natural position. The base also supports a first balloon which is also attached to back of the tube system, to control the relationship between the distal end of the tube system and the base. The base also serves as a supporting structure for tube system on which it rests.

The LFA can include one or more balloons positioned on the distal end of the LFA and along the tube system. The one or more balloons provide an airway seal and additionally can be used to align the distal end of the air tube.

In a further embodiment, the LFA can include a stylet to assist the insertion of an endotracheal tube. In a further embodiment, LFA can be configured in different size ranging from 2, 3, 4, 5 for use with different genders and ages. One skilled in the art of medical devices would be able to size the device for the standard sizes.

Further, alternatively, the LFA can include a removable handle coupled to the base and tube system. Preferably, a handle is not included because of the possibility of damage to the patient's teeth. The arrangement of those basic components of this invention, including but not limited to the EGDT, tube system including the air tube and fiber optic probe tube, balloon system, inflation injection line, interconnections between the balloons, or a combination thereof are still within the scope of this invention.

Tube System

The tube system comprises an air tube, a fiber-optic-probe tube, or a combination thereof. The air tube lumen and fiber-optic-probe lumen are not in communication. This prevents contamination of the fiber optic probe after each use and reduces the work of clearing and subsequently wear and damage of the probe during the clearing. The tube system is constructed with silicon like plastic material which provides a transparent view of an inserted endotracheal tube. By being able to view the endotracheal tube, an operator can to observe the fog of inside of an endotracheal tube once inside of tracheal, an indication that air is passing in and out of the lungs. The tube system can easily be flexed. Preferably, the tube system's unrestricted shape is preformed slightly ached with the tube system in front and the base at the back and will return to this configuration once the force is removed.

The length of the air tube can be sized for different ages, genders or types of animals. The tube system is of sufficient length to extend from the glottis opening to beyond the lips of a human or animal. The proximal end of the tube system can be configured with a bite guard that is sufficiently rigid to prevent a patient from biting down and cutting off or excessively restricting the communications through the air tube. The tube system can be formed out of materials with desired characteristics including but not limited to being relatively soft, elastic, forming smooth surfaces, and transparent or semi-transparent. Silicon rubber and preferably has a shore hardness of between 45-70 A is one such material.

In one embodiment, the proximal end of the tube system includes a coupling device, called an adaptor cap, to connect the air tube with industry standard 15 mm connector to medical devices including but not limited to an anesthesia circuits, breathing machines, resuscitation bag, respiratory treatment, or a combination thereof.

The tube system is a formed out of a flexible material that is preferably non-allergenic. Each tube within the assembled or formed tube system preferably provides a smooth channel for any instrument or other device to pass through. One skilled in the art of producing medical devices would be able to select the materials and techniques for manufacturing the tube system.

Preferably the distal end of the tube system is flexible so that the tubes can flex to follow the curvature of the person's or animal's tongue without excessive force.

The tube system includes an air tube and a fiber-optic probe tube. After proper LFA insertion, the distal end of both the air tube and fiber-optic-probe tube will face the front of the glottic opening. The proximal end of the air tube and the fiber-optic-probe tube will extend out the mouth and fit between the teeth. This segment or a portion of this segment can include a bite guard which is a thicker and is formed of relatively hard plastic material wrapping around the tube system and EGDT.

The air tube is open at both the proximal and distal ends. The air tube can carry air, oxygen, anesthesia gas, an endotracheal tube, a suction catheter or a combination thereof. The air tube is sized with internal dimensions sufficient for an endotracheal tube to freely pass through the air tube. Further, the air tube can be sized to further include a suction catheter to clean any blood or other secretions that may be around or near to the vocal cords or an oxygen supply to provide a patient with supplemental oxygen during intubation.

A cross section of the air tube preferably is not circler in shape. The diameter of its lower part can be bigger than upper part when the tube system is configured with a fiber-optic-probe tube and it is positioned to occupy the left upper corner of air tube. A suction or oxygen supply catheter or tube can follow a path just below the fiber optic probe tube and is part of air tube lumen. This path is spare space after an endotracheal tube is fit into the air tube. Further, the suction/oxygen supply channel does not communicate with fiber optic probe tube. This design allows the air tube has sufficient room for a suction catheter after an endotracheal tube is placed within the air tube.

The tube system can include a fiber-optic-probe tube. The fiber-optic-probe tube is open at the proximal end and closed at the distal end. The distal end is closed with a transparent covering that will transmit light and images substantially undistorted. The fiber-optic-probe tube is preferably smaller than the air tube and configured for a fiber-optic probe to be advance down to the distal end for viewing of the glottis opening and vocal cord area before, during, and after intubation. The air tube and the fiber-optic-probe tube are parallel to each other.

The tube system can include an adaptor cap that is coupled to or "capped" on the proximal end of the tube system. The adaptor cap is configured to have a 15 mm standard connector for connecting to a variety of devices, including a ventilator, an anesthesia circuit, a manual resuscitation bag, a breathing machine, a respiratory treatment device or a combination thereof. The adaptor cap of the tube system also has a separate connection port for fiber optic probe tube to avoid fiber optic probe being contaminated. The adaptor cap can include a pluggable hole, called suction/oxygen supply port. This hole allows either a suction catheter or a oxygen tube to be inserted into the air tube. An oxygen tube would be connected to an oxygen source during intubation whereas the suction catheter would be coupled to a suction device to suction out the secretion, bleeding or regurgitated gastric content before during and after intubation. If the LFA is used as a SGA, the adaptor cap includes a removable plug, call the suction/oxygen supply channel plug. This plug needs to seal the adaptor cap's oxygen/suction port for proper ventilation and can include an connecting wire or string between the plug and the cap.

During intubation, the adaptor cap will be removed to allow an endotracheal tube inserted into air tube. If LFA is to be used as an SGA, the adaptor cap is the oxygen/suction catheter port is plugged forming a substantially air tight seal and thereby preventing leakage during spontaneous ventilation and mechanic ventilation. Note, preferably the EGDT is separate from the tube system, is not connected with the adaptor cap, and preferably comes out the right side of the patients or animal's mouth.

Expansion Projections

The expansion projections provide three functions. First, they can help to keep a patient's airway open by holding back tissue that might be blocking a person's airway. Secondly, they can act as a guide directing a stylet or an ETT towards the laryngeal inlet. Thirdly, an expansion project can reduce the chance of aspiration when the bottom expansion projection is configured to rest on the top of the base's barb or other release mechanism. The bottom expansion projection resting against the base's barb creates a seal blocking aspiration of regurgitated gastric content.

In one embodiment, the tube system's distal end is configured with one or more expansion projections. The expansion projections are coupled to the periphery edge of the distal end of the air tube. Preferably, the projections are integrally formed as part of the end of the air tube or extension of the ending air-tube wall.

Further, in the preferred embodiment, there are four expansion projections located at a top, bottom, left lower corner, and right side of the distal end edge of the air tube. In an alternate embodiment there can be only three expansion projections on the right, and bottom and top. All projections are configured flexible and are formed so that when in a relaxed state they are orientated parallel with the longitudinal axis of the tube system or oriented inwardly slightly towards the center of the air tube. Thus, these projections can be directed towards the laryngeal inlet and provide a guide for the endotracheal tube during intubation and can push loose throat tissue out of the airway. The bottom, left, and right projections can be shaped as either a half circle, ellipse, prism, rectangular, sickle or combination thereof and can have different sizes and shapes. The projections should not have any sharp edges or corners. The top projection can have a round curved shape. Preferably, the expansion projections are made from the same material as the air tube's wall. Preferably, the one or more expansion projections should not be more than one inch long.

The top expansion projection is an extension of the top portion of the air tube wall. An expansion projection positioned on top of the air tube can lift the epiglottis when being released from restrained position. This expansion projection is also referred to as a first epiglottis elevation bar (EEB 1#). A second epiglottis elevation bar (EEB #2) is discussed later.

The expansion projections can be bent and folded inwardly towards the center of air tube and restrained in this position by a plastic barb or restraint means located near the end of the base. When the projections are restrained in this position, called a restrained position, the projections are to be restrained during LFA insertion. When the balloon system is inflated, all the projections are released from the barb or other means holding them in a restrained position. The all projections will release to a straight out relaxed position and help open the airway. Various restraining means are contemplated and discuses below in the section discussing the base.

In one embodiment, the bottom expansion projection is configured to rest on top of the barb located at the distal end of the base after release from the restrained position. When the first balloon (see section on inflatable balloon system) is inflated, all projections are released from restrained position. The bottom projection will be released from a folded restrained position and move over the top of the barb by its own elastic resilient force. The advantage of this configuration is that a better seal is created to prevent esophageal or gastric content regurgitation and to prevent aspiration of esophageal-gastric content into the laryngeal inlet. This serves as a secondary aspiration defense mechanism if the first defense fails. The first defense is the base tip blocking the upper esophageal opening and draining esophageal-gastric content by a drainage tube (EGDT). This drainage tube EGDT is discussed further below.

Epiglottis Elevating Bars

In an embodiment of the LFA, epiglottis elevating bars can be used to lift the epiglottis to exposure vocal cords, herein after EEBs. There can be two EEBs. The first EEB (EEB#1) is an expansion projection of the one or more expansion projections located at the top on the front end of the air tube.

The second EEB (EEB #2) is positioned inside the air tube lumen near the distal opening of the air tube. EEB #2 is a narrow long triangle shaped and is positioned very near to EEB #1 and also at the top of the air tube lumen. Before an ETT (endotracheal tube) advances through the air tube distal end, the EEB #2 rests inside and across all or part of air tube lumen, but is sized and configured not to block or overly restrict the air flow through the air tube lumen. As an ETT passes through the distal end opening of the air tube, the ETT will push EEB #2 forward and upward where a majority of the EE#2's length will extend out the distal end of the air tube lumen and preferably beyond the end of the EEB#1. The EEB#2 is configured to reach and lift the patient's epiglottis if the EEB #1 missed it which can occur in the case of short or small epiglottis. EEB #1 and EEB #2 function independently and are different in structure.

In one alternative embodiment, an EEB (hereinafter EEB#3), is located on top of and coupled to a cuff balloon. EEB#3 can be an alternative to EEB#1 and EEB#2 or can be used in combination with EEB#1 and EEB#2. EEB#3 can be formed of any semi-soft material including plastic, rubber, resin or a combination thereof. EEB#3 can be coupled to the cuff balloon by any means including but not limited to glue, thermal bonding, fasteners, or a combination thereof. The EEB can be flat or slightly curved. Preferably, the EEB#3 does not have any sharp edges or corners and is contoured to fit into the glossal epiglottis fold at the upper surface of the epiglottis.

Base

The base is preferably a flat substantially elliptic structure that can be made from a material with Shore hardness on the A scale of 50 or less and more preferably in the range of 25 to 40. Alternatively, the base can be other curved shapes and is preferably free of sharp edges and corners. The softness of the material functions as a cushion to reduce friction during the LFA insertion. After insertion, the back of the base sits against the back wall of the hypopharynx.

The proximal portion of the base is tapered into two branches or legs which weld smoothly with the back of the distal segment of the tube system. The base is coupled to the tube system by two bifurcation legs of the base and an esophageal-gastric drainage tube (EGDT). This EGDT first joins and attaches to the right side of the tube system at the bite guard. However, other positions for the EGDT are contemplated including positioning it along the left, top, or bottom side of the base. At the middle of the tube system, the EGDT separates from the tube system and attaches to the right top side edge of the base. Then the EGDC follows the curve of the distal end of the base to form the base tip. At the base tip is the EGDT distal end opening.

The anterior portion of the base is semi-ellipse shape. The posterior portion of the base gradually shape into two bifurcation legs, or branches, which then attach to the back of the tube system. The base and tube system together by means not limited to wielding, thermo fusion or pressure, glue adhesive, moldings or a combination thereof. When viewed from the back of LFA, one embodiment of the LFA can appear as one continuous smooth body.

Alternatively, the base can be manufactured in an injection mold process where the base and tube system are formed at the same time. A person skilled in the art of manufacturing injection molded medical devices would know the types of material and techniques for forming the base and coupling it with the tube system and having the desired physical characteristics.

The distal end of the base extends beyond distal end of the tube system. The distal portion of base is to be configured with a structure, a barb, hook, or other restraining device configured for an operator to fold the expansion projections behind the barb in an restrained configuration. The barb or restraining device is configured to restrain the expansion projections during insertion of LFA. While restrained, the expansion projections are held inwardly towards the axis of the tube system and preferable sufficiently folded inside of the recess of the barb. Thus, the expansion projections will not stretch out and catch on throat tissue, including the epiglottis, during device insertion.

The barb can be either an integral part of the base or an attachment to the base. Preferable, the barb is formed as part of the base. The barb is preferable formed of the same material as the base and is made of a flexible rubber or plastic material. The barb needs to be sufficiently flexible that the first balloon can readily push the expansion projections past the barb but stiff enough that the expansion projections are not release during LFA insertion into a patient's throat. A person skilled in designing medical plastic devices would pick a suitable material. Alternatively, the barb can be made of a different material and be hinged or flexibly coupled with the base. In such a configuration the barb can be non-flexible or not as flexible the base.

Further, the top surface of the barb can conformably fit with the shape of the bottom expansion projection. This can be a flat surface or a shaped surface to provide a better seal between the expansion projection and the barb. A good seal helps prevent aspiration of gastric content.

Other restraint means are contemplated include but are not limited to slots for the projections, snaps, and indentation or protrusions that engage with the restraint projections. The preferred restraining means is a barb.

The barb is configured such when balloon system inflated, the distal segment of the tube system is pushed upward from base, thus raising the distal segment of the tube system above the level of the barb. Subsequently, the two or more expansion projections will return from the restrained position to the relaxed position due to their elastic properties.

Preferable the base is coupled to the tube system such that in the restrained position, the base remains parallel with the tube system's longitudinal axis and held in close proximity to each other. This closeness is occurs when the first balloon is deflated. The first balloon is molded, wielded or adhesively coupled to the air tube distal wall adjacent to the base and to the adjacent base surface. The inflatable balloon system will be discussed below.

Inflatable Balloon System

The LFA can have one or more inflatable balloons. A balloon includes an inflatable structure that can surround a portion of another structure or is attached to another structure. A balloon can also be referred to as a cuff.

An inflatable balloon can provide multiple functions. First, a balloon can push soft tissue that might be found in an obese person aside to keep the airway open. Secondly, a balloon can form a seal between the distal segment of LFA and the wall of hypopharynx. Additionally, a balloon can be shaped so that different levels of inflation can change the position of the distal segment of the tube system's air tube for a better alignment with the glottic opening when the vocal cords deviate to the right or left. Further, an inflated a balloon can accommodate the contours and surrounding of the anatomic structures to stabilize the distal opening of the air tube in front of the glottic opening. Another function of the balloon is to release the expansion projections by pushing the distal end of the air tube upward and away from the base and thereby causing the base's barb to release the expansion projections.

The one or more balloons are in communication with one or more very small inflation tube, or called inflation line and injection port. When air, gas, oxygen or liquid injected into an inflation port and through an inflation line, the balloon will be inflated. The inflation injection port is configured such that the port has a self-sealing valve which can hold injected content without leaking out until an operator forcibly withdraws the injected content from the inflation injection port by using a syringe. Additionally, the balloon system can include a small indicator balloon, coupled by a small tube to one of the balloons, can be used as an indicator to estimate pressure inside the balloon system. Preferably the indicator balloon tube is connected with the cuff balloon to monitor its pressure because the cuff balloon is not directly inflated by the inflation injection tube. The tube coupling the indicator balloon with the cuff balloon can run along the left lower-outside wall of the tube system until reaching the bite guard. However, other paths are contemplated. Then this tube is detaches from the wall of the tube system and has sufficient length to extend outside of the lips of the patient. Finally, it connects with the indicator balloon.

Additionally, the balloon system can include a pilot balloon to provide a method of estimating the pressure within the first and the BSB. The pilot balloon can be coupled in-line with as part of the inflation line or injection port. Alternatively, the pilot balloon can be coupled to the first or BSB by a dedicated tube. One skilled in the art of designing medical parts would know how to form and manufacture a pilot balloon.

Preferably, inflation injection tube is flexible and is not attached to any structure at the proximal end. Preferably, it is coupled to the left lower side and outside of the tube system. Other paths of the inflation injection tube are contemplated. The inflation injection tube does not communicating with the air tube or fiber optic lumen of the tube system. However, other means of coupling the balloons to the inflation injection ports and tubes are contemplated. The balloons and inflation injection tube can be coupled by a separate tube or combination of tubes. In some embodiments, an inflation injection tube can be in communication with and control more than one balloon. Preferably, a syringe is used to inject gas or liquid into or pull them out, because a syringe can easily measure how much being injected in and how much being drawing out.

In present embodiment, there are three balloon connected each other. A first balloon is located between the back of distal end of the tube system and the base. The first balloon can be shaped like a wedge with the thicker end located just beneath the tube system's end opening. However, other shaped first balloons are contemplated including but not limited to a square, rectangular, a round or an irregular shaped balloon.

The BSB (Back Support Balloon), is preferably dome shaped after inflation. The first balloon is in communication with the BSB. The first balloon and BSB are together shaped like upside down saddle attaching along on the back of the distal segment of the tube system. The first balloon and BSD preferably can appear like one balloon with anterior and posterior chamber. The communication between the anterior and posterior chamber is restricted by a relatively narrow connection between the two balloons. This connection is preferably also coupled to the back of the tube system by molding, wielding, thermopressue, adhesive glue or any other suitable technologies.

Inflation of the first balloon causes an anterior movement of the distal end of the tube system. Therefore, inflation of the first balloon can be used to align or better align the end opening of the distal air tube with the laryngeal inlet. Additionally, the first balloon causes sufficient movement to separate the base and the tube system distal end. This separation causes the barb to release the airway expansion projections upon which they will resume their relaxed straight-out positions.

The second balloon, also referred to as the cuff balloon, forms a cuff around a segment of the tube system's distal end. The cuff balloon covers the left, right, and top side of the tube system's distal end and the right and left side of the first balloon. In this embodiment, the right, left, and top side of the cuff balloon are in communication with each other. The cuff balloon communicates with first balloon by a small plastic compressible tube, called the first-cuff balloon communication tube. The first-cuff balloon communication tube allows the gases or liquids to flow from the first balloon into the cuff balloon at a low rate. This delayed inflation in the cuff balloon will first provide that the first balloon raise end edge of tube system and release the one or more expansion projections and then inflate the cuff balloon to push surrounding soft tissue away and create a clear passage for an advancing endotracheal tube.

The cuff balloon's preferred embodiment requires an adjustable volume of air, oxygen, other gas, or liquid to inflate the cuff balloon. In one embodiment, the first-cuff balloon communication tube is configured to run under the left side of the cuff balloon, which is between the cuff balloon and the left side of air tube wall, before it connects with the cuff balloon. When the gases or liquids flowing into the cuff balloon and pressure inside of the cuff balloon increase to predetermined level, the expanded cuff balloon will compress or cut off the first-cuff balloon communication tube to stop more gases or liquids from flowing into the cuff balloon. The pressure inside of the cuff balloon is design to be lower than the first balloon. This provides a self-adjusting pressure mechanism. By only accepting a certain amount volume and predetermined pressure for the cuff balloon, the possibility of over expansion of the cuff balloones is minimized and therefor surrounding fragile soft tissue distortion and damage is minimized as well. And because this mechanism, the adjustable pressure inside the cuff balloon provides the cuff balloon that easily accommodates local anatomy and can move the air tube into better alignment position with the glottic opening.

In a further embodiment of the invention, the BSB is located and attached to the back side of the tube system wall of near the middle segment and rests on the posterior hypo-pharyngeal wall before inflation. The first balloon and BSB freely communicate by a relatively narrow connection providing a low flow rate providing for a delayed inflation of the BSB but is configured such that both the first balloon and the BSB reach the same pressure. Alternatively, another inflation line to BSB can be used for inflation. After the BSB is inflated, the BSB will push against the hypo-pharyngeal wall which causes the LFA to move anteriorly. Then subsequently, the LFA will push the back of the tongue upward and anteriorly. This action will make the distal portion of the tube system better aligned with the laryngeal inlet.

There are advantages for having a lower pressure in the second balloon. First, the lower pressure makes the cuff balloon smoothly accommodate the contour of surrounding laryngeal structures while still pushing excessive soft tissues away. Further, the lower pressure is very unlikely to cause any harm to laryngeal structures. On the other hand, BSB and first balloon needs higher pressure to raise the distal portion of the tube system to align with the laryngeal opening. Further, if an operator decide to use LFA as a superglottic airway without tracheal intubation, by partially deflating the first balloon and subsequently the BSB, the LFA may be used for a longer duration surgery as a superglottic airway device without uncomfortable tension within the airway, and at same time keeps the low pressure cuff balloon inflated to provide a seal and prevent air leak during spontaneous or mechanic ventilation.

The first balloon and the BSB is usually made of a rubber like material such as, for example, nature rubber, synthetic rubber, and elastomer in the form of flexible tubular membrane. The cuff balloon can be formed out of synthetic resin material including but not limited to polyethylene, polyester, non-rigid polyvinyl chloride, silicon resin, polyurethanes, or a combination thereof. Preferably, the cuff balloon is softer than the first and third balloon.

Stylet

A stylet is a guiding device for inserting an endotracheal tube and locating the laryngeal opening. The device consists of a flexible rod, or a shaft, and a semi-soft but very resilient sickle shaped distal tip. The rod needs to be longer than an endotracheal tube which is longer than the LFA. On the distal end of the rod, is a soft and flexible sickle shaped tip with a shore hardness of 35-45 A. The rod is made of a relatively more rigid material than the tip and preferable has a Shore hardness of 45-55 A.

The sickle shaped distal tip is configured with sufficient flexibility to be moved around the laryngeal inlet without damaging any tissue until the gap between the vocal cords is found. The surface of the sickle shaped tip is very slippery either by a coating polytetrafluoroethylene (PTFE) material or is made of very low coefficient of friction materials.

The stylet tip has a number of important angles and curves that are important in its use in finding the laryngeal inlet. The stylet's sickle shaped tip is comprised of a first tip segment, a second tip segment, and a tip. First, the first tip segment angles from the rod at between 20 to 45 degrees down from where the first tip segment connects to the rod. The first tip segment continues from this point to a point that can be wider than an ETT. Because of the tip's flexibility, it can be still be slid down and pulled out from an EET.

The second angle is between the first tip segment and the second tip segment. The first tip segment and second tip segment preferable form an angle of between 110-150 degrees. The second segment is preferably slightly curved. However, greater curvature is contemplated for the second segment. The tip, located at the end of the second tip segment is round, smooth, and slippery. These features will make the sickle shaped tip move away from areas of high resistance and more readily move to the areas of least resistance which is the laryngeal opening. The sickle shaped tip will also help to guide an endotracheal tube through the vocal cords and prevent the endotracheal tube from hanging up on and damaging the vocal cords.

This stylet tip shape and these limitations provide several benefits. First, it allows for the stylet to be slid down an endotracheal tube. Secondly, when the stylet is rotate, the tip will move around a wider area for locating of the laryngeal inlet. Once in the laryngeal inlet, the curvature of the tip can help guide the ETT into the trachea.

The stylet can be used in conjunction with the LFA device. Before the LFA insertion, an endotracheal tube can be placed in the air tube. The stylet is placed into the endotracheal tube. The stylet sickle-shaped tip is designed to flexibly move around, or "looking for", the laryngeal inlet. Once the tip has "found" and passed between the vocal cords into the tracheal, an operator can feel tracheal ring by either the angle point or the sickle shaped end point of the stylet. Then endotracheal tube is advanced, following the stylet to and through the vocal cords.

Another stylet characteristic that enables it to readily find the laryngeal opening is that the material forming the first tip segment and the second tip segment can be formed such that the stylet tip has substantially uniform flexibility in any direction.

Alternatively, the stylet can be inserted into the LFA's air way tube without an endotracheal tube. Once the stylet is inserted into the trachea, the LFA is withdrawn and an endotracheal tube slid along the stylet into the trachea.

Alternatively, embodiments of the stylet can be used in combination with other airway devices, including but not limited to a laryngeal mask airway or intubation laryngeal mask airway.

The material from which the tip can be constructed is any suitable plastic material; as selected by the material specialist. Latex free medical grade silicone rubber is one preferred material. Other suitable material for construction of this type of device include, but no limited to, Polytetrafluoroethylene (PTFE), Polyvinyl Chloride (PVC), Thermoplastic Elastomers such as the styrene copolymers (e.g. Styrene Butadiene styrene SBS), Styrene Ethylene Butylene (TPO), Thermoplastic poly-Urethanes (TPU), Co-polyester (COPE), Polyether Block Amides (PEBAX) and foamed version thereof, where appropriate. Also, the material used to construction of the tip should have very slippery surface with coefficient of friction between 0.05 to 0.1. Due to its flexibility and very slippery properties, an operator can easily move the tip around within the laryngeal inlet, changing directions and rotating it to find a lower resistance area such as laryngeal inlet by manipulating the shaft of the stylet.

Operational Example

In operation the LFA device is first prepared for insertion. The stylet is inserted into an ETT (endotracheal tube) lumen. The sickle-shaped tip of the stylet is extended beyond the ETT's distal end opening. Then the endotracheal tube can be lubricated and inserted into the air tube or as mentioned above or can have only the stylet inserted into the LFA without an endotracheal tube. The balloon system is deflated, so the tube system and the base will be in close proximity to each other. The one or more expansion projection are tucked under the barb of the base. The LFA is well lubricated. An operator will use one hand to open the mouth and will use the other hand to insert LFA into the mouth. Then an operator uses one or two fingers push down the middle segment of LFA to flex the LFA to follow the curvature of the middle line of natural curvature of the hard palate, soft palate and pharynx until the LFA reaches the proper position. Proper position can be where the leading edge of the base is press against a person's upper esophageal sphincter. At this position, the resistance will be felt by the operator. Additionally, the operator can reference depth marks along the of tube system to estimate the LFA's placement in the throat.

After LFA is in a proper position, an operator will start injecting air gas or liquid into the balloon injection port to inflate the first balloon. The inflated first balloon will raise the end of tube system and release the one or more expansion projections. One of the projections on the top of air tube is EEB #1. The EEB #1 will likely be positioned under the epiglottis, or may be positioned in a glosso-epiglottic fold at the upper surface of the epiglottis after it is released from the barb. In either position, the raising of EEB #1 will lift the epiglottis up which opens the glottic inlet.

As the first balloon inflates, the cuff balloon subsequently inflates. The cuff balloon will push the excessive soft tissue surrounding glottic inlet away to create a clear passage for an endotracheal tube passing through, especially in case of obese patients. The inflated cuff balloon also form a seal around the glottis opening. When LFA used as supraglottic airway (SGA), the air seal by the cuff balloon will allow spontaneous ventilation or low pressure positive ventilation without air leakage. Because the cuff balloon is low pressure balloon and has self-limited pressure or pressure cut-off mechanism, it will accommodate a variety of the anatomic cavities without excessive pressure to surrounding tissue.

The BSB will be inflated after first balloon inflates which will push against the wall of oral pharynx and hypo-pharynx and therefore the tube system will push back anteriorly. This anterior and upward movement of the tube system will subsequently move the tongue anterior and upward toward oral cavity. This action will also straighten to a certain extent the distal segment of air tube and better align it with the glottic opening. Optionally, a fiber optic probe can be inserted to monitor the positioning of air tube, the endotracheal tube and vocal cord area.

The pressure in the first balloon can be adjusted by injection of more or less air which adjusts the height of end the tube system for alignment of the air tube with the glottic opening. When drawing air, gas or liquid out of first balloon, the BSB will be deflated in slower pace and cuff balloon will be even more slowly deflated due to the soft narrow first-cuff communication tube under compression by the cuff balloon.

Next the stylet and an endotracheal tube together are advanced gently along the air tube. The advancing endotracheal tube can raise the EEB #2 resting on the inside of the distal opening of the air tube. The raised EEB #2 will raise the epiglottis if the EEB #1 missed the epiglottis. This can occur in the case of a short and small epiglottis. At same time the sickle tip of the stylet slides around with the operator feeling for the least resistance area which would be laryngeal opening. Once the tip of stylet passes though the vocal cord, the hand of operator will feel the loss of resistance. Pushing the stylet further down, an operator may feel tracheal ring.

The depth marks on the stylet also can also be used as reference. Because the esophageal opening is blocked by the tip of base, the end opening of air tube is aligned with laryngeal inlet and positioned close to the front of laryngeal inlet. Therefore, the sickle tip of the stylet can only be advanced and passed through vocal cord into tracheal.

After the stylet is inserted into the tracheal, the endotracheal tube is slide down into the tracheal. Then the stylet is withdrawn and the balloon system is deflated.

Next step is removal of the LFA without pulling out the endotracheal tube. An operator's one hand holds the LFA and another hand pull out the stylet. Now operator can use one hand to gradually slide out the LFA along the stylet and another hand to hold the shaft of the stylet firmly against the endotracheal tube moving out the LFA leaving only the ETT in the tracheal.

Alternatively, the stylet can be put into the lumen of an air tube without an endotracheal tube. Once the LFA is in proper position and the balloon system is inflated, the stylet is advanced to locate the laryngeal inlet by gently rotating the stylet. Also, this location process can be performed by moving the proximal end of the tube system slight up and down, left and right, which will cause the sickle tip of the stylet to move in the opposite direction, and at the same time the other operator's hand pushing of the stylet. This gentle wiggling action does not create breaking or bruising of the surrounding soft tissue. This is because the tube system is surrounded by the soft cuff balloon and the first balloon. The balloons filled with compressible air, gas or liquid have sufficient cushioning and provides the end of tube system room to move.

Once the stylet finds and slides into laryngeal opening, the hand of operator pushing the stylet will suddenly feel loss of resistance. Then the balloon of LFA is deflated and LFA is slid out patient's or animal's mouth along the stylet. Then an endotracheal tube is slid in along the stylet into the patient or animal's mouth, past the vocal cord and slid into the patient or animal's trachea. Then the stylet will be pulled out and an ETT remains in the trachea.

In an optional step, a suction catheter is inserted in the proximal opening of the air tube and pushed beyond the distal opening of the air tube. The air tube can be sufficiently large enough to contain an endotracheal tube and a suction catheter. During the intubation or after intubation, the patient can easily have blood or secretions suctioned out. If an endotracheal tube is not used, then the suction catheter can easily be inserted down more into the tracheal to suction out secretion or blood. Additionally, the suction catheter can be connected to an oxygen supply and used as a tool for oxygen delivery through the LFA during intubation. Further, an fiber optic probe tube can be inserted into the air tube lumen or the endotracheal tube for viewing the vocal cord area.

In a further optional step, if the LFA used as a SGA, the balloon system can be inflated to the point where air stops leaking. The air leakage can be heard if an operator puts their ear close to the patient's or animal's mouth. This can limit the possibility of excessive pressure on the hypo-pharynx tissue during a long surgery. The small pilot balloon can be coupled to the first balloon and used to indicate the pressure inside of the first balloon and BSB balloon. An indicator balloon can be coupled to the cuff balloon and used to determine or approximate the pressure inside of the cuff balloon. Alternatively, after inflating the balloon system, an operator's hand can feel fullness at super thyroid notch area which may suggest that the cuff balloon being full inflated.

To reduce the pressure in the balloon system, the operator can withdraw some air or fluid from the injection port, this will deflate the first balloon. Because there is small narrow compressible first balloon communication tube, air inside of the cuff balloon will flow back to the first balloon in very slow pace. This mechanism will keep the pressure inside of cuff balloon relatively stable and keep the seal for spontaneous ventilation or artificial ventilation.

In a further step, the proximal end of the EGDT can connected with a suction device or a regular oral gastric tube can be passed through the EGDT into the stomach then connecting to a suction device. An adaptor cap can be put on the proximal end of LFA having a standard fifteen (15) mm connector. This allows connection to but not limited to an anesthesia circuit, ventilator, respiratory treatment machine.

Referring to FIG. 1, an exploded embodiment of the LFA 10 is shown and described. The base 400 has an elliptically shaped front end tapering to two tails 440. The shown embodiment has a barb 433 for restraining the base's expansion projections 211 (also referred to EEB#1), 212, 213, 214 and the EEB#2 215 at the end of the air tube. Coupled to the base is the balloon system 100, and the tube system 200. The base 400 is coupled to the tube system 200 along the base 400, preferably along the two tails 440. Further, the esophageal gastric drainage tube (EGDT) 330 is coupled to the end of the base 400 with the opening 320 centered on the base tip.

The balloon system 100 was described above. The shown embodiment includes an inflated cuff balloon 73', an inflated first balloon 86', and an inflated BSB (Back Support Balloon) 74'. An inflation tube 90 couples the injection port 70 to the first balloon 86' The first balloon 86' is in communication with the BSB 74' through a low rate connection 82 to provide a delayed inflation. The cuff balloon 73' is in communication with the first balloon 86' through a first-cuff tube 95 that runs between the cuff 73' and the tube system 200. See the balloon system section above of details on how the balloons can be connected and limits the inflation pressure. Further, the inflation tube 90 can include a pilot balloon 92 used to indicated the pressure in the first balloon.

A pressure indicator 71 is coupled to the cuff balloon 73' through a tube 91. The indicator can be a balloon which an operator can gently squeeze to judge the pressure or a calibrated device showing a relative pressure or can include both.

The tube system 200 is coupled to the balloon system 100 and base 300. The tube system distal end is saddled by the cuff balloon 73'. The shown embodiment of the tube system 200 is comprised of an air tube 201 and a fiber-optic-probe tube 121, and expansion projections 211, 212, 213, and 214. An EEB#2 215 is coupled at the top distal end of the air tube lumen 203. A bite guard 240 is formed at the proximal end of the tube system. The characteristics of the bite guard 240 are described above in the section on the Tube System.

The adaptor cap 500 adapts industry standard equipment to the tube system 200. The cap has a fifteen millimeter standard connector adaptor 502 that provides unrestricted communications between the air tube lumen 203 and an anesthesia circuit or other respiratory device. One skilled in the art of building medical equipment would know the physical requirements for an industry standard fifteen millimeter adaptor. The cap 500 includes a port 506 for inputting an oxygen/suction catheter (not shown). The port 506 can be sealed with a plug 504 which can be connected to the cap by a string, when the LFA 10 is being used as a SGA. The connector 508 provides access to the fiber-optic-probe lumen 120—FIG. 4 through the cap lumen 510. Details of the use of the cap are described above within the section on the Tube System.

Figure 2A:
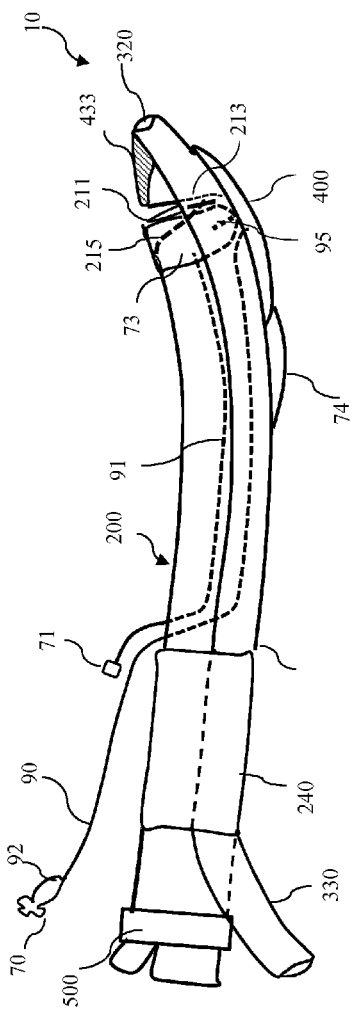
FIG. 2A is a side view of the first LFA embodiment with the balloons deflated.

Referring to FIG. 2A, a side view of the LFA device 10 is shown and described. The LFA device 10 can includes an adaptor cap 500 connected to the tube system 200, a base 400 that includes a barb restraint device 433, expansion projections 211, 212, 213, 214, and a EET#2 215, and a EGDT (esophageal gastric drainage tube) 330 through which an oral gastric tube can be inserted and pass through the distal opening 320. The LFA 10 further includes and a cuff balloon 73, a first balloon 86 (not shown here), and a BSB (back support balloon) 74.

The tube system 200 can include an air tube 201 and a fiber-optic-probe tube 121. The adaptor cap 500 provides a connection between standard breathing machines (not shown), suctioning machines (not shown), or a combination thereof to the air tube 201.

The distal end of the tube system 200 is shown configured with four expansion projections, 211, 212, 213, 214. The projections 211, 212, 213, 214 and EEB 215 are flexed inward towards the air tube distal opening which are held in place by a barb restraint means 433.

An inflation port 70 is coupled to an inflation tube 90 which is coupled to a first balloon 86 which is shown deflated. A first-cuff tube 95 runs under the cuff balloon 73. The cuff balloon 73 is also shown deflated. Details of the balloon system and the first-cuff tube 95 are described in detail above in the "Balloon System" section.

An EGDT 330 runs along the right side of the tube system 200 and then along the top of the base 400 and terminating with an opening 320 at the distal end of the base 400. The proximal end of the tube system 200 can connect into the adaptor cap 500.

Figure 2B:
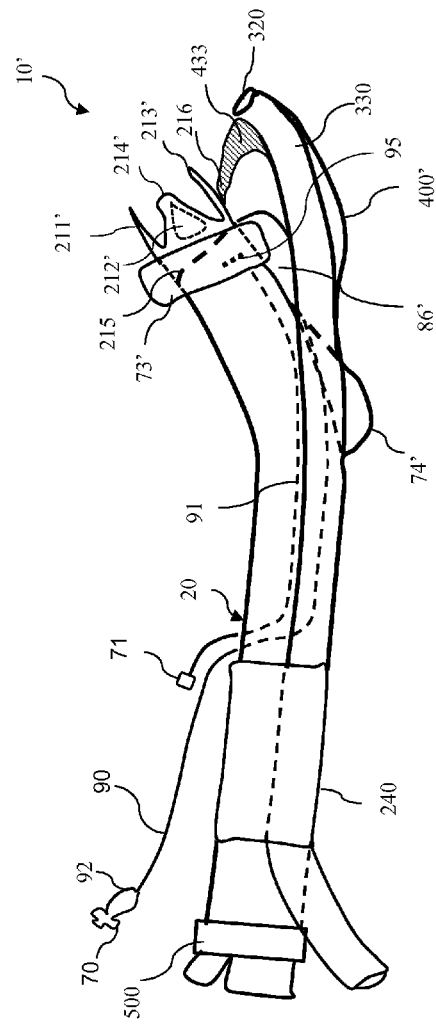
FIG. 2B is a side view of the first LFA embodiment with the balloons inflated.

FIG. 2B is an illustration the LFA device 10' embodiment with the balloons 73', 74', and 86' inflated. The distal end of the tube system 200 is flexed upward and apart from the base 400 by the inflated first balloon 86'. The expansion projections 211', 212', 213', and 214' are released from the barb restraint 433. The bottom expansion projection 213' rests on top of the barb restraint 433. This barb 433 and expansion projection 213 provides a seal 216 that help prevents gastric leakage from being aspirated. Details of the tube system and associated components are described above in the Tube System and Balloon System sections.

The back support balloon 74' is shown inflated which when properly positioned in a patients throat presses against the back of the throat.

The cuff balloon 73' inflates from a first-cuff tube 95 between the first balloon 86 and the cuff balloon 73. This first-cuff tube 95 is a soft flexible tube that is configured to collapse when a predetermined amount of external pressure is placed against it. The first-cuff tube 95 is mounted on the air tube 201 outer wall. As the cuff balloon 73 inflates, the pressure in the cuff balloon 73' places pressure on the first-cuff tube 95. When the pressure between the inflated cuff balloon 73' and the air tube 201 outer wall reaches a predetermined level, then the soft flexible tube 95 collapses thereby halting further air or fluid flow into the cuff balloon 73'. This self-regulation means of the cuff balloon's 73 pressure prevents the over inflation and thus damage to a patient's throat tissue. A pressure indicator 71 is shown coupled to a tube 91 coupled to the cuff balloon 73'. More details of the balloon system can be found above in the section "Balloon System".

Figure 3A:
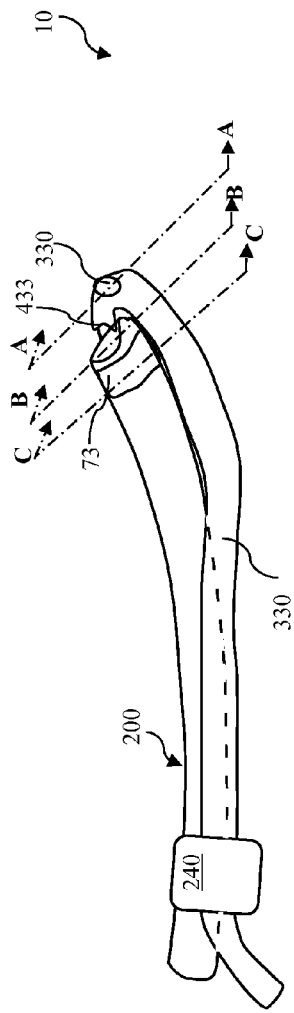
FIG. 3A is a side view of the multiple cross sections of the first LFA embodiment with the balloon system deflated.
Figure 3B:
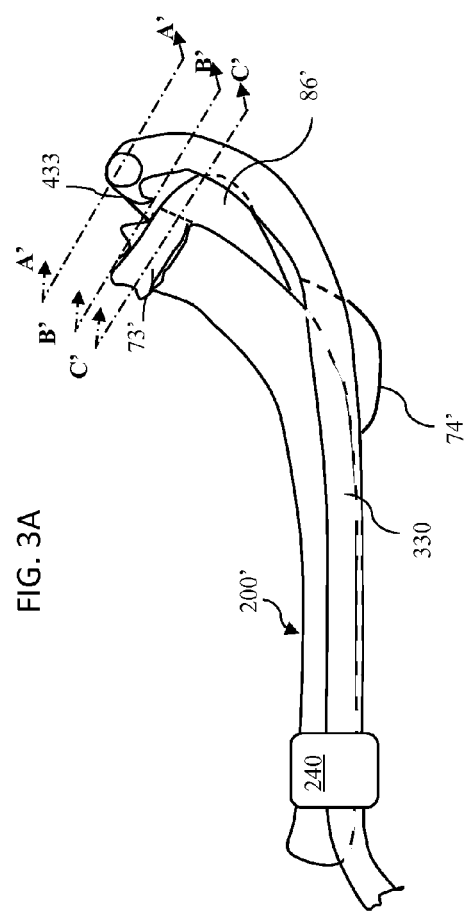
FIG. 3B is a side view of the multiple cross sections of the first LFA embodiment with the balloon system inflated.

FIG. 3A is a side prospective view of first LFA 10 embodiment with the balloons 73, 74, 86 deflated and FIG. 3B with the balloons 73', 74', 86', inflated. Cross sectional views A, B, and C are indicated through the LFA 10 bisecting the balloon system 100-FIG. 1, tube system 200, and base 400.

Figure 4A:
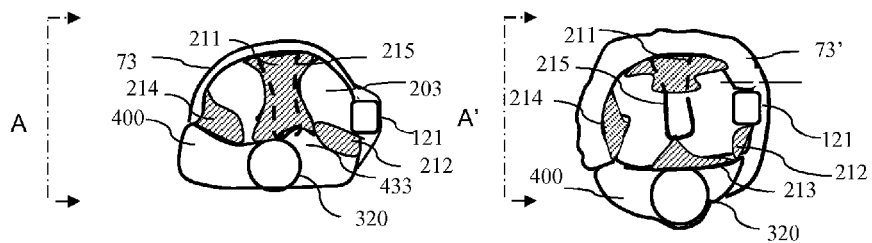
FIG. 4A is cross section front view through the first LFA embodiment tip.

FIG. 4A is a view from a cross section A of the first LFA 10 embodiment's base tip. The figure on the left is a cross section of the LFA 10 with the balloon system deflated and the figure on the right is a cross section of the LFA 10 with the balloon system inflated. The EGDT distal end opening 320 is centered at the tip of the base 400.

Four expansion projections 211, 212, 213, and 214 (hidden) are shown flexed over the air tube opening 203 being restrained by the barb 433.

In the left figure, the four expansion projections 211, 212, 213, and 214 are shown restrained by the base barb 433. The expansion projections 211, 212, 213, and 214 are flexed towards the center of the air tube lumen 203. The EEB 215 is shown hidden behind the expansion projection 211. Note that expansion projection 211 can also be an EEB and was described above as EEB#1.

The figure on the right shows a cross section A' of the LFA 10 with the balloon system inflated. The expansion projections 211', 212', 213', 214' are extending substantially straight out. The cuff balloon 73' is shown inflated and the base 400 pushed and separated from the air tube. The EEB 215 can be seen extending across the air tube.

Figure 4B:
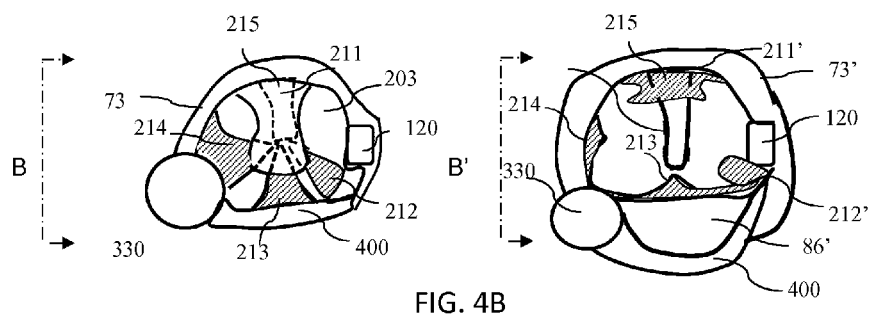
FIG. 4B is cross section front view through the first LFA embodiment in front of the expansion projections.

FIG. 4B is a cross section B of the first LFA embodiment 10 in-front of the expansion projections with the balloon system deflated and the balloon system inflated.

In the figure on the left side, the cuff balloon 73 is deflated. The EGDT tube 330 is seen on the left side. The expansion projections 211, 212, 213, and 214, are shown restrained. The EEB#2 215 is shown behind the top expansion projection 211 (also referred to as EEB#1).

The right figure shows the cross section with the first balloon 86' and cuff balloon 73' inflated. The expansion projections 211, 212, 213, and 214 are in a relaxed configuration and extending towards the viewer. The EEB#2 215 can be seen extending down from the roof (top inside) of the air tube 201.

Figure 4C:
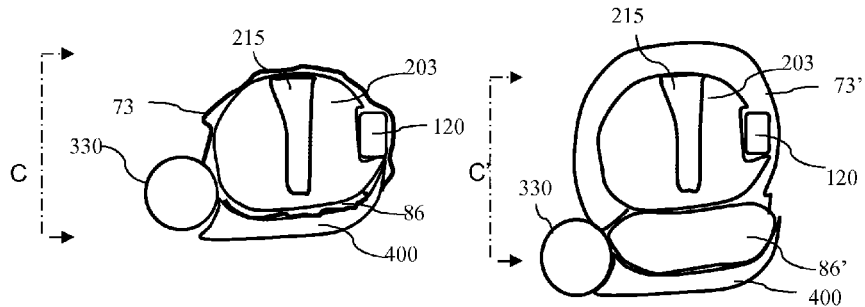
FIG. 4C is cross section front view through the first LFA embodiment cuff balloon.

FIG. 4C is a cross section C of the first LFA embodiment 10 though the cuff balloon of with the balloon system deflated and the balloon system inflated. In this cross section, the EEB#2 can be seen in its relaxed state extending into the air tube lumen 203.

In the left figure, the cuff balloon 73 is deflated. The EGDT tube 330 is seen on the left side. The EEB#2 215 is shown extending into the air tube lumen 203. The EEB#2 can extend all the way across or partially across the air tube lumen 203. The width of the EEB#2 should be limited such that sufficient air can pass through the air tube lumen 215 when the LFA 10 is being used as a SGA. Further details on the EEB#2 are found in the above description on the tube system.

In the right figure, the cuff balloon is shown inflated. The base 400 and tube system are shown pushed apart by the first balloon 86'. The EEB#2 is shown in the same position as the when the cuff balloon 73 is deflated.

FIG. 5A depicts the part of the LFA structure that auto-limits the pressure in the cuff balloon 73. The first balloon 86 and the cuff balloon 73 are shown deflated. The first balloon 86 and the cuff balloon 73 are coupled by a first-cuff tube 95 which is a soft resiliently collapsible tube. The cuff balloon 73 is shown wrapping part of the way around the first balloon 86. However, a cuff balloon 73 that wraps further around the first balloon 86, less, completely, or not at all around the first balloon 86 is contemplated by this invention.

The first-cuff tube 95 is positioned, either all or part of the tube, between the outer wall of the air tube 201 and the cuff balloon 73. However, the first-cuff tube 95 can run between the outer wall of the air tube 201 or any other tube system 200 outer wall and the cuff balloon 73.

The first-cuff tube 95 is configured to be in communications between the first balloon 86 and the cuff balloon 73 when the external pressure on the tube 95 created between the cuff balloon 73 and the air tube outer wall 201 is below a preconfigured pressure. This pressure is the result of the pressure within the cuff balloon 73. When the first balloon 86 is filled with air, the air flows into the cuff balloon 73 and thereby inflates the cuff balloon 73.

FIG. 5B depicts the LFA structure that auto-limits the pressure in the cuff balloon 73' after the cuff balloon 73' inflates to a predetermined pressure. Because the cuff balloon 73' is inflated though the first balloon 86', the first balloon is shown inflated. The first-cuff tub 95' is shown collapsed with the communications between the first balloon 86' and the cuff balloon 73' closed by the pressure between the cuff balloon 73 and the wall of the air tube wall 201. If more air is injected into the cuff system, the pressure in the first balloon 86' can be higher than the cuff balloon 73' because the first-cuff tube 95 is collapsed and thereby stopping further communication between the two balloons. When air is removed from the first balloon 86', the LFA 10 pressure against the throat tissues is reduced, and thereby reducing the pressure in the cuff balloon 73'. Accordingly, the first-cuff tube 95 reopens and the air within the cuff will flow out.

Referring to FIG. 6, another embodiment of the adaptor cap 500A is shown. The adaptor cap 500A adapts industry standard equipment to the tube system 200 while providing access for a fiber-optic probe without contamination from the airway tube, and access for either a suction catheter or an oxygen supply catheter while the LFA being used as a superglotic airway. The cap 500A has a fifteen millimeter standard connector adaptor 502A that provides unrestricted communications between the air tube lumen 210 (not shown) and an anesthesia circuit or other respiratory device. One skilled in the art of building medical equipment would know the physical requirements for an industry standard fifteen millimeter adaptor. The cap 500A includes a sealable port 506A for inputting an oxygen/suction catheter (not shown). The port 506A can be sealed with a plug 504A which can be connected to the cap by a string, when the LFA 10 is being used as a SGA. The connector 508A provides access to the fiber-optic-probe tube 121. Details of the use of the cap are described above within the section on the Tube System.

Figure 7:
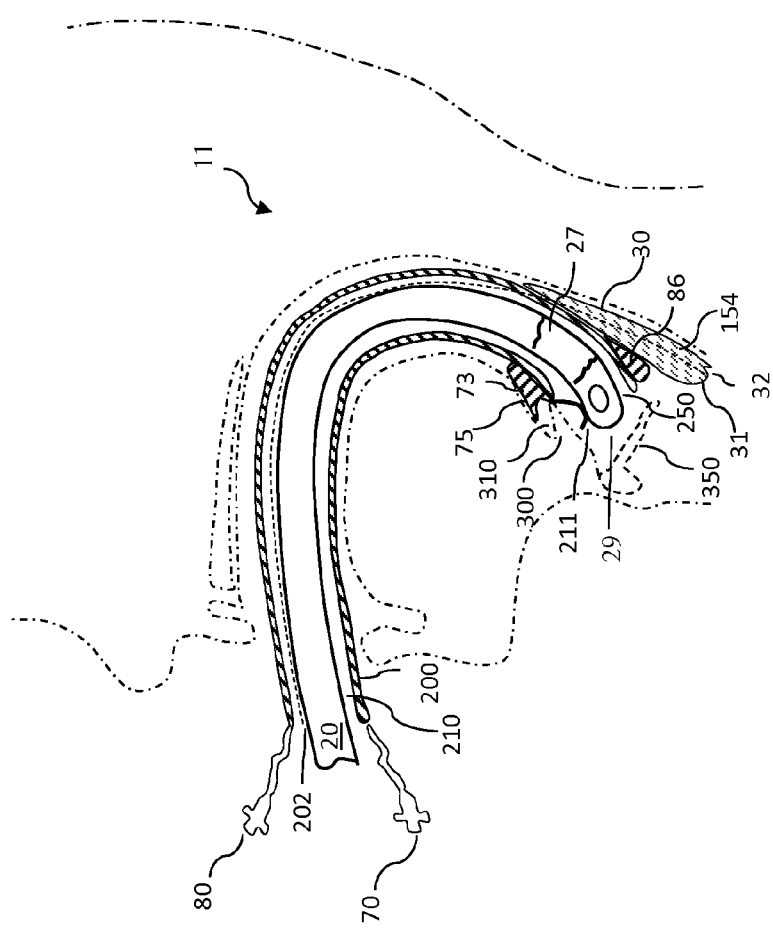
FIG. 7 is a left side cross-sectional view of the second LFA embodiment inserted into a person's mouth and throat.

Referring to FIG. 7, an embodiment of a left-side longitudinal cross-section view of a second LFA 11 embodiment is shown inserted into a person's throat. The cross-section transects the air lumen 210. Passing through the air lumen 210 an endotracheal tube 20 is shown extending through the air tube 200 from the proximal opening 202 to the air tube distal opening 250. The end of the endotracheal tube 29 is shown engaging a second EEB 215.

A first inflation balloon 86 is shown inflated. The inflated first balloon 86 moves the proximal airway opening 250, and the end of the endotracheal tube 29 in alignment with the vocal cords 350 in a patient's airway. The first inflation port 80 is shown at the proximal end of the tube system 15. The first inflation port 80 is coupled to the first inflation balloon 86 by a lumen, a tube or other means (not shown).

The cuff inflation balloon 73 is shown inflated and positioned in the glosso-epiglottic fold 310. A epiglottis elevation bar 75, described above as EEB#3) is positioned on top of the cuff balloon 73 and lifting the epiglottis 300 away from blocking the laryngeal opening. The second inflation port 70 is shown at the proximal end of the tube system 15. The second inflation port 70 is coupled to the cuff balloon 73 by a lumen (not shown).

The base 30 is shown coupled to the back side of the tube system 15. The end of the base system 31 can be engaged with the oral-gastric sphincter (not shown). The base 30 is configured with an oral-gastric channel 154 with an opening 32 at the tube system distal end. The channel extends from the proximal end of the tube system to the distal end of the base 31.

Figure 8:
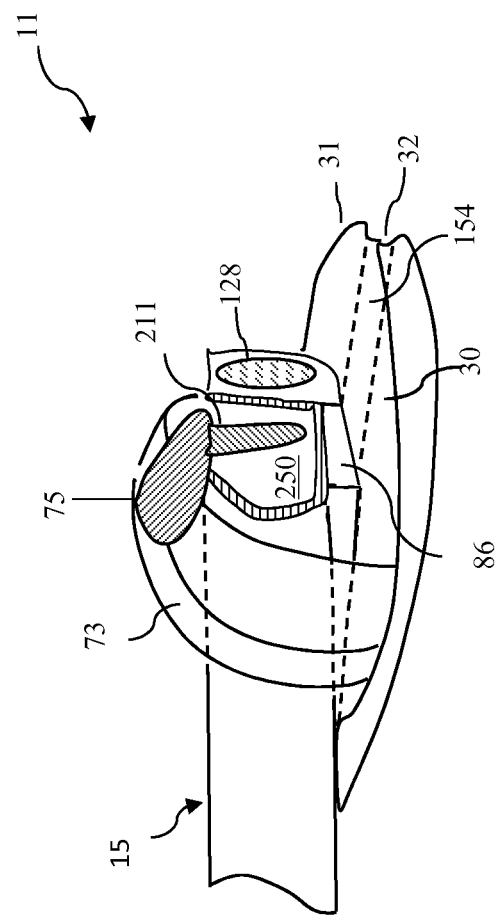
FIG. 8 is an upper perspective view of the distal end of a second LFA embodiment.

Referring to FIG. 8, a top oblique view of the distal end of a second LFA 11 embodiment is shown and described. The air tube opening 250 is seen and the end transparent covering 128 of fiber-optic-probe tube is shown on the far side of tube system 15.

A cuff balloon 73 is shown wrapping around the distal segment of the tube system 15. A first inflation balloon 86 is shown attached to the base 30 but in other embodiments can be attached to the tube system 15. A first balloon 86 is shown between the base 30 and the tube system 15 distal segment. A first epiglottis elevation bar 75 is shown attached to the top of an inflated first cuff balloon 73. In the shown embodiment, a bar 75 covers substantially the top of the tube system 15 but other sized elevation bars 75 are contemplated. A second epiglottis elevation bar 211 is shown attached at or near to the air tube end 250. The embodiment of the base 30 is shown with an oral-gastric-tube channel 154 in the base 30 back with the oral-gastric channel end 32 at the distal end of the base 31.

Figure 9:
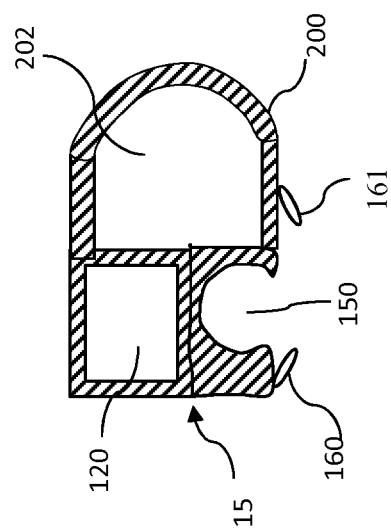
FIG. 9 is a view of the proximal end of the second LFA embodiment.

Referring to FIG. 9, a proximal end view of and alternative embodiment of the tube system 15 is shown and described. The proximal fiber-optic-tube opening 120 is shown along with the proximal air tube opening 202. The proximal gastric-tube-channel opening 150 is shown below the fiber-optic-tube opening 120. Two buckles 160, 161 are shown proximally located on the tube system 15 bottom side.

Figure 10:
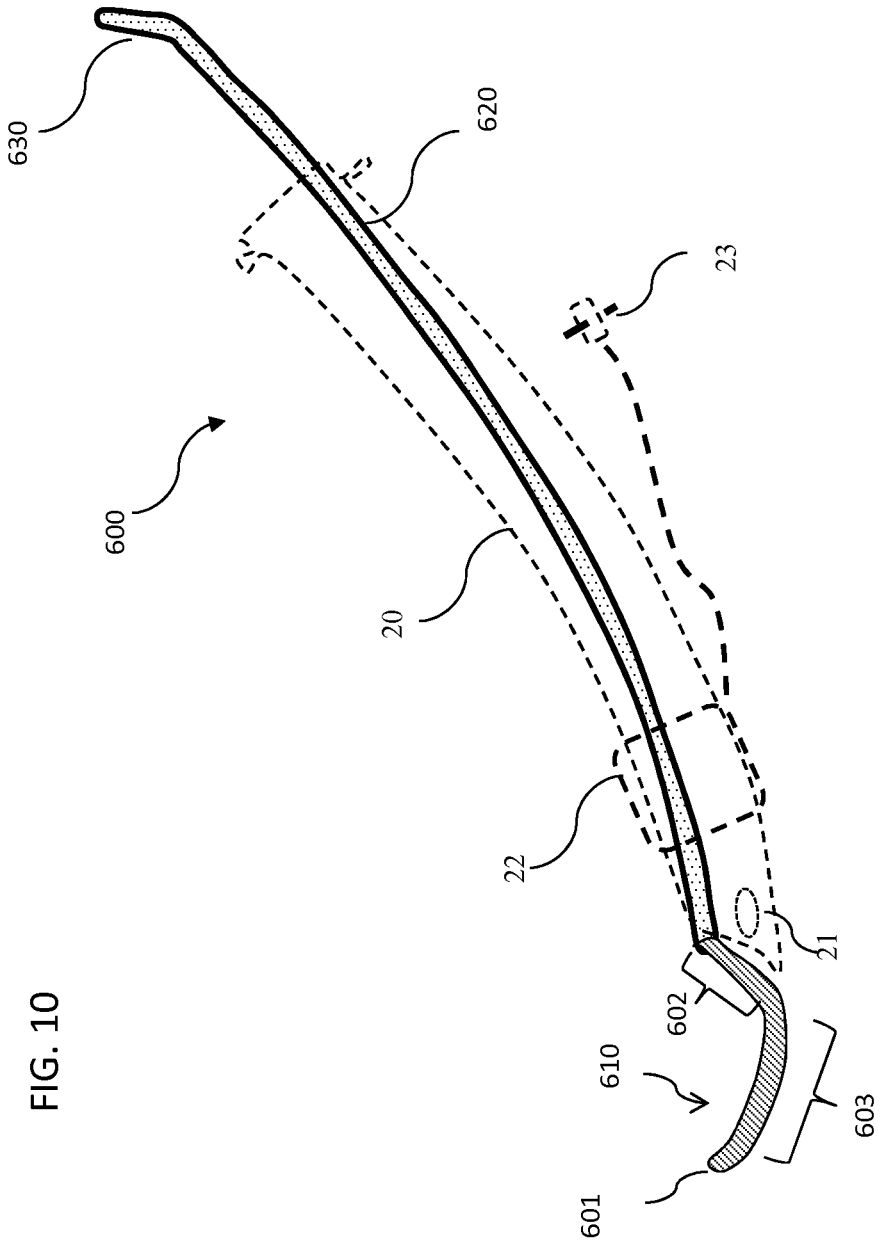
FIG. 10 is a side view of the stylet inserted into a intubation tube.

Referring to FIG. 10, a side view of an embodiment of the stylet 600 inserted into an endotracheal tube 20 is shown and described. The endotracheal tube 20 includes an aperture 21 inflation cuff 22 and an injection port 23.

The stylet 600 is comprised of a proximal end 630, a shaft 620, and a sickle shaped tip 610. The shaft 620 is flexible and can be made out of a material that can be easily cleaned and autoclaved. The sickle shaped tip 610 is preferable made from a slippery and flexible resilient material. The proximal end 630 can be bent at between 20-40 degrees and is between a half of an inch long and an inch and one half.

The stylet 600 sickle shaped tip 610 can include a tip 601, a first tip segment 602, and a second tip segment 603. Preferable these segments 602, 603 are made from the same material. The first tip segment 602 and second tip segment 603 preferable form an angle of between 110 to 150 degrees. The second tip segment 603 is slightly curved towards the axis of the shaft 620 forming a sickle shape. The sickle tip 601 is very smooth and preferably round. These features enable the sickle shaped tip to move, slide, or spring away from areas of resistance when the tip 610 engages with tissues in the area of the laryngeal opening until reaching the laryngeal opening where the resistance is lost. This change of resistance is detectible by an operator using the stylet through the shaft 620. The proximal end 630 can be used to help turn the sickle tip 610. Further, the sickle shaped tip 610 provides a guide for an endotracheal tube 20 through the vocal cords which thereby prevents the endotracheal tube from hanging up on the vocal cords. The bend at the proximal end 630 can be used to remove the stylet 600 once the endotracheal tube 20 is inserted past the vocal cords.

The stylet tip 610 has two bend points, one where the tip 610 meets the shaft 620 and the second where the first tip segment 602 meets the second tip segment 603. Preferable the sickle shaped tip 610 has substantially equal flexibility at each of the bend points.

What is claimed is:
1. An airway device comprising:
a tube system comprising an air tube having, a tube system distal segment, an air tube distal end, forming an air tube distal opening, and an open air tube proximal end and forming an air tube lumen, and a fiber-optic-probe tube having an open fiber-optic-probe tube proximal end and a close fiber-optic-probe tube distal end forming a fiber-optic-probe lumen, wherein the air tube is open at a distal and proximal ends, wherein the fiber-optic-probe tube is open at a proximal end and closed on the distal end, and wherein the distal end is transparent to light and transmits substantially distortion free images;
a base coupled to the tube system distal segment and wherein the base includes a base leading edge configured to press against an upper esophageal sphincter, and a restraint means; and
one or more expansion projections connected to the air tube distal end, wherein one expansion projection of the one or more expansion projections is positioned at the top of the air tube distal end and is configured as a first epiglottis elevation bar wherein the first epiglottis elevation bar is configured to resiliently flex from a restrained position over the air tube distal opening to a released position, and wherein the restraint means is configure to hold the first epiglottis elevation bar in the restrained position.

2. The device of claim 1, further comprising a second epiglottis elevation bar wherein the second epiglottis elevation bar is coupled to the inside of the air tube distal end and extends substantially across air tube lumen, wherein the second epiglottis elevation bar is configured to lift an epiglottis when inserted into a patient's or animal's throat with the base's tip positioned against the patient's upper esophageal.

3. The device of claim 2, wherein the second epiglottis elevation bar is longer than the first epiglottis elevation bar and extends beyond the first epiglottis elevation bar when raised by an endotracheal tube or a stylet passed through the air tube distal end lumen.

4. The device of claim 3, wherein the fiber-optic-probe tube is coupled to the air tube along the longitudinal axis without communication between said air tube lumen and said fiber-optic-probe tube lumen, wherein said fiber-optic-probe tube is configured to accept a fiber-optic-probe.

5. The device of claim 4, further comprising an adaptor cap, wherein the adaptor cap is configured with a fifteen millimeter connector, a sealable aperture, and a fiber-optic probe port, wherein the fifteen millimeter connector is in communication with the air tube, wherein the sealable aperture is in communication with the air tube and configured to accept an oxygen or a suction catheter.

6. The device of claim 1, wherein the one or more expansion projections includes a left expansion projection, a right expansion projection, and a bottom expansion projection, wherein in a relaxed state the left, right, and bottom expansion projection are orientated parallel to the air tube's longitudinal axis and wherein the expansion projections are configured to guide an endotracheal tube or stylet towards the patient's or the animal's laryngeal inlet when the tube system distal opening is adjacent to the patient's or the animal's laryngeal inlet.

7. The device of claim 1, further comprising a first balloon, wherein the first balloon is located between the base and the tube system distal segment, and wherein said first balloon is configured to separate the tube system distal segment from the base.

8. The device of claim 7, wherein the base further comprises a restraint means for the one or more expansion projections and wherein the restraint means is configured to hold the one or more projections positioned in front of the air tube's distal opening.

9. The device of claim 8, wherein said restraint means is configured so that the when first balloon is inflated the restraint means releases the one or more projections from said restraint means.

10. The device of claim 9, wherein one expansion projection of the one or more expansion projections is a bottom expansion projection configured at the bottom of the air tube, and wherein said bottom expansion projection is configure so that when the first balloon is inflated said bottom expansion projection is released from the restraint means to a position on top of the restraint means and thereby providing a seal between the bottom expansion projection and the restraint means.

11. The device of claim 10, wherein the restraint means is a barb.

12. The device claim 11, wherein the barb is configured and made of materials with flexibility and rigidity, wherein flexibility allows the bottom expansion projection to slide over the top surface of the barb, and wherein the rigidity allows barb to hold the bottom expansion projection in front of the distal end of the air tube before releasing it.

13. The device of claim 7, further comprising a cuff balloon, wherein the cuff balloon covers a segment of the tube system's distal end, wherein the first balloon and the cuff balloon surrounds the tube segment, and wherein the first balloon and the cuff balloon are configure to provide a seal in a patient's throat when inflated.

14. The device of claim 13 where the first balloon and cuff balloon are in communication through a collapsible communication tube, wherein the collapsible communication tube is positioned between the tube system's outer wall and the cuff balloon, and wherein the collapsible communication tube is configured to cut off communication between the first balloon and the cuff balloon when the cuff balloon is inflated to a pre-configured pressure, and wherein said collapsible communication tube will resume communication when the cuff balloon is deflated.

15. The device of claim 14, further comprising an epiglottis elevation bar, wherein the epiglottis elevation bar is coupled to the top of the cuff balloon.

16. The device of claim 13 further comprising a pressure indicator and an indicator tube coupling the pressure indicator with the cuff balloon.

17. The device of claim 14, wherein the cuff balloon is configured to generate a sealing force to close said collapsible communication tube and its communication capability when the cuff balloon is inflated to a preconfigured pressure and thereby enabling the cuff balloon to be filled to a lower pressure than the first balloon.

18. The device of claim 7, further comprising a back support balloon, wherein the back support balloon is coupled to the tube system back, and wherein the first balloon and the back support balloon are in communications through a narrow passage.

19. The device of claim 1, further comprising an esophageal-gastric drainage tube, wherein the esophageal-gastric drainage tube runs from the distal end of the base towards the proximal end of the tube system, wherein the esophageal-gastric tube is configured to receive an oral gastric tube or configured to operate as an independent esophageal-gastric drainage means.

20. The device of claim 19, wherein the distal end opening of said esophageal gastric tube is configure as the base tip while said esophageal gastric tube is configured to couple the base to the tube system.

21. An airway device comprising:
a tube system comprising an air tube and a fiber-optic-probe tube, wherein the air tube is open at a distal and proximal ends, wherein the fiber-optic-probe tube is open at a proximal end and closed on the distal end, and wherein the distal end is transparent to light and transmits substantially distortion free images;
a base coupled to the tube system distal end and wherein the base is configured for the leading edge to press against an upper esophageal sphincter;
an esophageal gastric drainage tube running from the base distal leading edge to the proximal end of the air tube;
one or more expansion projections connected to the air tube distal end;
a first balloon, wherein the first balloon is located between the base and the tube system distal end;
a restraint means for the one or more expansion projections and wherein the restraint means holds the one or more projections bent in front of the air tube's distal end opening;

a cuff balloon, wherein the cuff balloon covers a segment of the distal end of the tube system, wherein the first and the cuff balloon surround the tube system, and wherein the first and cuff balloon are configured to provide a seal in a patient's or animal's throat when inflated;

a back support balloon wherein the back support balloon is coupled to back of the tube system; and a collapsible first-cuff balloon communication tube configured between the cuff balloon and the tube system outer surface.

22. An airway device comprising:

a tube system having a longitudinal axis, a tube system proximal end, a tube system distal segment and a tube system distal segment end;

a base having a base proximal end, wherein the base proximal end is only coupled to the tube system distal segment, wherein the base is substantially parallel with the longitudinal axis of tube system, and wherein the base extends beyond the tube system distal segment end; and an inflatable balloon system, wherein the inflatable balloon system is configured to have one or more balloons, wherein the one or more balloons are configured to hold the tube system distal segment and the base adjacent to each other when the inflatable balloon system is deflated and is configured to change position of the tube system distal segment, relative to the base, when the inflatable balloon system is inflated.

23. The airway device of claim 22, wherein the base proximal end includes two bifurcation legs coupled to the tube system.

24. The device of claim 22, wherein said inflatable balloon system includes more than one balloons and one or more inflation injection tubes in communication with the one or more balloons.

25. The device of claim 22, wherein said balloons are configured to be inflated at different rates.

26. The device claim 22, wherein the base is configured to couple to the tube system and to couple to an esophageal gastric drainage tube, wherein the esophageal gastric drainage tube also functions as a connection between the tube system and the base.

* * * * *